(12) United States Patent
Venturini Del Greco

(10) Patent No.: US 10,973,864 B2
(45) Date of Patent: Apr. 13, 2021

(54) ENZYME-ASSISTED LIPID-BASED EXTRACTION AND STABILIZATION OF PHYTO-CANNABINOIDS AND TERPENS AND PRODUCTS OBTAINED THEREOF

(71) Applicant: HERBOLEA BIOTECH S.R.L., Sesto Fiorentino (IT)

(72) Inventor: Giovanni Venturini Del Greco, Florence (IT)

(73) Assignee: HERBOLEA BIOTECH S.R.L., Sesto Fiorentino (IT)

( * ) Notice: Subject to any disclaimer, the term of this patent is extended or adjusted under 35 U.S.C. 154(b) by 6 days.

(21) Appl. No.: 16/477,968

(22) PCT Filed: Jan. 15, 2018

(86) PCT No.: PCT/EP2018/050860
§ 371 (c)(1),
(2) Date: Jul. 15, 2019

(87) PCT Pub. No.: WO2018/130682
PCT Pub. Date: Jul. 19, 2018

(65) Prior Publication Data
US 2020/0061136 A1 Feb. 27, 2020

Related U.S. Application Data

(60) Provisional application No. 62/446,429, filed on Jan. 14, 2017, provisional application No. 62/524,239, filed on Jun. 23, 2017, provisional application No. 62/546,372, filed on Aug. 16, 2017.

(51) Int. Cl.
*C12N 9/24* (2006.01)
*A61K 36/185* (2006.01)
*A61K 31/352* (2006.01)
*C12P 7/22* (2006.01)
*C12P 17/06* (2006.01)

(52) U.S. Cl.
CPC .......... *A61K 36/185* (2013.01); *A61K 31/352* (2013.01); *C12P 7/22* (2013.01); *C12P 17/06* (2013.01)

(58) Field of Classification Search
CPC ....................................................... C12N 9/24
See application file for complete search history.

(56) References Cited

U.S. PATENT DOCUMENTS 9,895,404 B1 2/2018 Baskis
2017/0106030 A1 4/2017 Aari et al.

OTHER PUBLICATIONS

PCT International Search Report and Written Opinion for PCT/EP2018/050860, dated Apr. 17, 2018.
Wu et al., "Optimization of enzyme-assisted solvent extraction technology of cannabidiol from hemp leaf," China Brewing, 35:79-82 (2016).
Kitryte et al., "Biorefining of industrial hemp (*Cannabis sativa* L.) into cannabinoid and antioxidant fractions by high pressure and enzyme-assisted extraction," 1st Food Chemistry Conference, Oct. 30-Nov. 1, 2016, Amsterdam Poster programme, pp. 1 and 8.
Kitryte, et al., "Biorefining of industrial hemp (*Cannabis sativa* L.) into cannabinoid and antioxidant fractions by high pressure and enzyme-assisted extraction," 1st Food Chemistry Conference, Oct. 30-Nov. 1, 2016, Amsterdam Poster, p. 1.
Kitryte, et al., "Biorefining of industrial hemp (*Cannabis sativa* L.) threshing residues into cannabinoid and antioxidant fractions by supercritical carbon dioxide, pressurized liquid and enzyme-assisted extractions," Food Chemistry 267:420-429 (2017).
Herbolea, "Unique bio-processing technologies," Bio-Herbolysis information retrieved from http://www.herbolea.com/take-action pp. 1-4.

*Primary Examiner* — Rosanne Kosson
(74) *Attorney, Agent, or Firm* — Troutman Pepper Hamilton Sanders LLP (Rochester)

(57) ABSTRACT

The present application provides a safe, efficient, environmental friendly and convenient method for an enzyme assisted lipid-based extraction and stabilization of phyto-cannabinoids and terpenes/terpenoids from plant materials. The lipid-based extract presents high cannabinoid content and enhanced phyto-cannabinoids and terpenes/terpenoids stability, and it can be valorized toward multiple applications in the health, cosmetic, food and agricultural sectors.

13 Claims, No Drawings

ENZYME-ASSISTED LIPID-BASED EXTRACTION AND STABILIZATION OF PHYTO-CANNABINOIDS AND TERPENS AND PRODUCTS OBTAINED THEREOF

This application is a national stage application under 35 U.S.C. § 371 of PCT Application No. PCT/EP2018/050860, filed Jan. 15, 2018, which claims the priority benefit of U.S. Provisional Application Ser. No. 62/446,429, filed Jan. 14, 2017; 62/524,239, filed Jun. 23, 2017; and 62/546,372, filed Aug. 16, 2017.

BACKGROUND

Cannabis refers to a genus of annual herbaceous plants in the Cannabaceae family. Humans have cultivated Cannabis throughout recorded history as a source of industrial fiber, seed oil, food, and medicine, and for religious, spiritual and recreational purposes.

Although the main psychoactive constituent of Cannabis is tetrahydrocannabinol (Δ9-THC), the plant is known to contain more than 400 compounds, among them at least 60 cannabinoids. Besides THC, another cannabinoid produced in high concentrations by some plants is cannabidiol (CBD). CBD is considered to have a wide scope of potential medical applications—due to clinical reports showing the lack of side effects, particularly a lack of psychoactivity (as is typically associated with Δ9-THC), and non-interference with several psychomotor learning and psychological functions. In addition to cannabinoids, hemp or cannabis contain various terpenes such as terpineol, limonene, myrcene, terpinolene, humulene and sesquiterpenes. When terpenes are modified chemically, such as by oxidation or rearrangement of the carbon skeleton, the resulting compounds are generally referred to as terpenoids. All cannabinoids are terpenoids, but not all terpenoids are cannabinoids. Terpenes and terpenoids, including cannabinoids, are generally nonpolar substances and hence soluble in lipids. Some authors use the term "terpene" more broadly, to include terpenoids.

Terpenes display unique therapeutic effects that may contribute meaningfully to the entourage effects of cannabis-based medicinal extracts. It has been hypothetized that some terpenes could attenuate undesirable effects of THC (Russo, 2011). Terpenes, not cannabinoids, are responsible for the aroma of cannabis. Monoterpenes usually predominate (limonene, myrcene, pinene), but these headspace volatiles (Hood et al., 1973), while only lost at a rate of about 5% before processing (Gershenzon, 1994), do suffer diminished yields with drying and storage (Turner et al., 1980; Ross and ElSohly, 1996), resulting in a higher relative proportion of sesquiterpenoids (especially caryophyllene), as also often occurs in extracts.

The synergetic interaction of different cannabinoids and terpenes is known as the 'entourage effect' introduced in cannabinoid science in 1998 by S. Ben-Shabat, with Raphael Mechoulam, to represent a novel endogenous cannabinoid molecular regulation route.

The endocannabinoid system consists of the endogenous cannabinoids (endocannabinoids), cannabinoid receptors and the enzymes that synthesise and degrade endocannabinoids. Many of the effects of cannabinoids and endocannabinoids are mediated by two G protein-coupled receptors (GPCRs), CB1 and CB2, although additional receptors may be involved. CB1 receptors are present in very high levels in several brain regions and in lower amounts in a more widespread fashion. These receptors mediate many of the psychoactive effects of cannabinoids. CB2 receptors have a more restricted distribution, being found in a number of immune cells and in a few neurones. Both CB1 and CB2 couple primarily to inhibitory G proteins and are subject to the same pharmacological influences as other GPCRs. Thus, partial agonism, functional selectivity and inverse agonism all play important roles in determining the cellular response to specific cannabinoid receptor ligands.

By interating with the endocannabinoid system, exogenous cannabinoids, such ones from cannabis, are used to reduce nausea and vomiting during chemotherapy, to improve appetite in people with HIV/AIDS, and to treat chronic pain and muscle spasms. Cannabis, its constituent cannabinoids, and terpenes are used to treat diseases or improve symptoms. Cannabinoids are under preliminary research for their potential to affect stroke or children's epilepsy.

Cannabis sativa L. is a prolific, but not exclusive, producer of a diverse group of isoprenylated resorcinyl polyketides collectively known as cannabinoids (Hanuš et al. 2016) nor cannabinoids from cannabis are the only lipid based exogenous compounds interacting with the endocannabinoid system. In the last few years, other plants have been found to produce cannabinoid-like compounds and several non-traditional cannabinoid plant natural products have been reported to act as cannabinoid receptor ligands.

Consequently as 'phyto-cannabinoid' is described any plant-derived natural product capable of either directly interacting with cannabinoid receptors or sharing chemical similarity with cannabinoids or both. (Gertsch et al., 2010).

Among phyto-cannabinoids different from traditional cannabis' cannabinoids, that have been reported to interact with the endocannabinoid system, unsaturated fatty acid N-alkylamides (N-alkylamides) from the medicinal plant Echinacea, a species of herbaceous perennial plant in the family Asteraceae, have been demonstrated to bind to the CB2 receptor more strongly than the endogenous cannabinoids (Raduner et al., 2006 and Woelkart et al., 2005). The interaction of N-alkylamides with the endocannabinoid system as been proven to modulate induced immune response. Other constituents from Echinacea purpurea act as weak CB1 antagonists (Hohmann et al., 2011).

Salvinorin A, a diterpene in Salvia divinorum, produces CB1-mediated effects in the gastrointestinal tract of rodents. Salvinorin A primarily acts as a kappa-opioid receptor agonist and is inactive as a ligand for CB1 and CB2 (Capasso et al., 2008); it may interact with a putative CB1-kappa-opioid receptor heterodimer (Fichna et al., 2012).

Bitter acid humulone, a terpenoid contained in Humulus lupulus (hops) of the same Cannabinaceae family, is thought responsible for sedative effect. Humulone is subject to degradation in about 12 weeks at room temperature (Darby, 2015). Interestingly in 2017, Isodiol, a biotech company claimed it has extracted CBD from modified strains of hops.

Hyperforin is also a terpenoid produced by St. John's wort (hypericum perforatum). Cannabinoids, bitter acids and hyperforin are polyketides with terpenoid building blocks and are lipophilic due to their terpenoid moiety (Osburn and Lanzotti, 2009).

Pyrethrins are terpenoids produced by Chrysanthemum genus plants. Pyrethrins can be found in cannabis plant material and extracts as pyrethryns are used in the formulation of natural pesticides for cannabis protection. Interestingly, in 2017, Devitt-Lee et al. reported the possibility that pyrethrins may be endogenously synthetized by cannabis, hence they could become an additional component of cannabis extractable phyto-complex.

Among plants producing cannabinoid-like compounds, *Helichrysum umbraculigerum*, a South-African species of everlasting is also a major producer of CBG (Bohlmann et al., 1979). Other plants containing cannabinoids-like compounds are the Chinese rhododendron and liverwort Radula Marginata in New Zealand (Toyota et al., 2002).

Various patents and scientific publications are available providing different dosages of phyto-cannabinoids for disease or symptoms treatment. For instance, dosage in the range of 10-20 mg/kg/day of CBD are envisaged to treat epilepsy (GB2548873). For a 50 kg weight person, that would mean 500-1.000 mg/day of CBD. Assuming a 4% concentration of CBD in the extract, that would require the daily assumption of 12.5-23 ml of extract. In case of 0.5% concentration of CBD in the extract, the dosage of extract would be in the range 100-200 ml, a quite significant quantity to be consumed on a daily base.

Various processes to extract phyto-cannabinoids and/or terpenes/terpenoids have been developed. The following major extraction processes are known:

1. Cold pressing for producing hemp seed oil. Hemp seed oil is rich in nutrients and is a good addition to any diet, but only contains small amounts of cannabinoids (<2%, in the case of industrial hemp), as it is made from just the seeds of the plant. Hemp seed oil can certainly be added to CBD supplements as a base for these products. However, cold pressing is not useful to produce an oil high in cannabinoids, as cannabinoids are mostly contained in the stalks and buds that cannot be directly processed by a normal press or expeller.

2. The Rick Simpson Method for Cannabis Oil is a popular extraction method for extracting CBD oil, which uses petroleum or naphtha as solvents. This method, although efficient in extracting the active compounds from the cannabis plant (mostly done with plants high in THC), usually leads to products that have a lower concentration of terpenoids and other cannabinoids such as CBD, while effectively yielding higher concentrations of THC. The main drawback of such method is that residuals from the solvents may remain and potentially interfere with one's immune function as described by Romano and Hazekamp ("Cannabis Oil: chemical evaluation of an upcoming cannabis-based medicine", 2013).

3. Extraction with ethanol can be used for extracting the full range of cannabinoids from the cannabis plant, and it is safer than the Rick Simpson method. On the other hand, ethanol has a low selectivity and it extracts undesired chlorophyll and waxes, so the final product has an unpleasant taste. Chlorophyll can be removed by filtering the extract, but this additional step also removes a significant proportion of the cannabinoids, therefore leading to less potent extract. Furthermore, stability of cannabinoids as well as N-alkylamides in ethanol extracts is low (Citti et al., 2015 and Spelman, 2009).

4. Extraction with Sonication/ultrasonic waves: C. Da Porto, (Ultrasound-assisted extraction of volatile compounds from industrial *Cannabis sativa* L. inflorescences, 2014) describes procedures for extracting THC and terpenes from hemp by using ultrasonic waves. The use of ultrasonic increased the extraction of THC, but after 15 min of treatment the overall efficiency of extraction was still not satisfactory.

5. Super Critical $CO_2$ extraction (U.S. Pat. No. 9,186,386 B2, U.S. Pat. No. 6,403,126 B1) can be an efficient method to obtain a highly-enriched cannabinoids oil (>60%). At such level of concentration, the product is not directly consumed but it is diluted with vegetable oils such as olive oil to reach 3-5%. The method uses safe solvents, but it requires complex equipment and expertise, in addition to be high-energy demanding, thus the product obtained is very expensive making the potential health benefits obtainable thanks to the therapeutic use of cannabinoids not accessible to all. Additionally, it requires the initial cannabis material to be dried, adding a step that is time consuming and has negative effects on important compounds such as volatile monoterpenes. Furthermore, the process itself is subject to significant losses in terms of monoterpenes extraction yield, hindering the entourage effect of the extracts. Additionally, it has high selectivity for toxic components which might be present in pesticides, therefore a risk associated to their presence in concentrated form in the final product might be present. Moreover, the product of $SC-CO_2$ extraction may have a significantly different chemotypic fingerprint from that of cannabis flower (Sexton, 2017). Finally, the stability of cannabinoids extracted with $CO_2$ diluted in olive oil is inferior to that obtained with their direct extraction in olive oil as described by Cannazza ("Medicinal cannabis: Principal cannabinoids concentration and their stability evaluated by a high-performance liquid chromatography coupled with diode array and quarupole time of flight mass spectrometry method", 2016).

6. Extraction with microwaves. Koturevic et al. (A rapid method for the extraction of cannabionoids from *Cannabis sativa* using microwave heating technique, 2014) described the possibility to use microwaves to assist the extraction of cannabinoids by organic solvents. Few organizations such as New Brunswick Innovation Research Chair in Medical Technologies (NBIRC), Radient Technologies and Scientus Pharma announced partnerships with cannabis producers to develop microwaves-assisted cannabinoids extraction methods. Technical data are still limited, nevertheless technical limitations might derive from the step of separation of solvent from plant material, the recovery of solvent that remains adsorbed in the vegetable matrix, the ratio solvent to plant material and, finally, the possibility to reach high concentration in extracts in case non-volatile solvents are used (i.e. vegetable oils).

7. Romano-Hazekamp method is based on the extraction of cannabinoids from pre-heated, dried cannabis inflorescences using vegetable oils (i.e. olive oil) as solvents. The method can be used for extracting the full range of cannabinoids from the cannabis plant and it has the advantage of being very safe for consumption. Furthermore, it is considered the most sustainable process from an environmental point of view. (Cannabis Oil: chemical evaluation of an upcoming cannabis-based medicine, Luigi L Romano, Arno Hazekamp, 2013). The drawbacks of this simple and increasingly popular method are that in order to achieve a satisfactory cannabinoids extraction yield, the extraction with vegetable oils has to take place at 98° C. for a prolonged time (1-2 h) and the quantity of oil to be added as solvent to the plant material is from 4 to 10 times the quantity of plant material, accordingly the level of cannabinoids content in the oil achievable is less than 1% and more than 50% of volatile mono-terpenes is lost due to prolonged high temperature treatment. Finally, the stability of cannabinoids in the vegetable oil is very low, with a degradation in just two weeks of over 15% and over 20% for storage at 4° C. and ambient temperature respectively, as described by Pacifici ("Evaluation of cannabinoids concentration and stability in standardized preparations of cannabis oil by ultra-high performance liquid chromatography tandem mass spectrometry", 2017).

8. Steam distilling and hydro-distillation are traditional methods for monoterpenes extraction. Steam distilling involves suspending a basket of herb above a vessel of boiling water. The steam passes through the perforated basket and penetrates the plant material. Only volatile compounds such as monoterpenes are soluble in the steam. Hydrodistillation is similar to steam distilling except that the herb is placed directly in the boiling water. The methods are not suitable for non-volatile substances such as cannabinoids or heavier terpene compounds.

Thus, it is necessary for new and more efficient processes to be developed for extracting and stabilizing lipophilic phyto-cannabinoids and/or terpenes/terpenoids, even from newly harvested plant material, using green and/or food grade solvents or excipients, such as vegetable oils or other such lipids.

SUMMARY OF THE INVENTION

Provided herein is a process useful for an enzyme assisted lipid-based extraction of lipophilic cannabinoids and/or terpenes/terpenoids from plant material, such as hemp, cannabis, hops, echinacea, salvia dinivorum, chrysanthemum, helichrysum and hypericum biomass. Thus, in an aspect, provided herein is a process for producing a lipid-soluble extract from plant material containing phyto-cannabinoids and terpenes/terpenoids, comprising the steps of:
  a. comminuting the plant material;
  b. mixing the comminuted plant material with enzymes to form a mixture to which water and lipids are optionally added;
  c. agitating the mixture at a temperature range of 1 to 80° C.; and
  d. separating the mixture into a lipid phase, an aqueous phase, and a solid phase;
  wherein the lipid phase comprises the lipid-soluble extract.

The process according to the present invention may be carried out by proceeding with steps a. and b. only, preserving the mixture resulting from step b. and proceeding with the the addition of lipids and separation step d. subsequently, with or without agitation of the mixture. The separation step d. can be carried out after one or more days, even in a different laboratory or facility.

In another aspect, provided herein, is a lipid-soluble extract obtainable from the process according to the invention, wherein the extract has a total phyto-cannabinoid content of at least 2, 3, 4 or 5 weight percent.

In yet another aspect, provided herein, is a lipid-soluble extract obtainable from the process according to the invention, wherein the ratio between the two main cannabinoids in the lipid-soluble extract differs for less than 10%, preferably less than 5%, the ratio between the two main cannabinoids in the plant material.

In yet another aspect, provided herein, is a lipid-soluble extract obtainable from the process according to the invention, wherein less than 10%, preferably less than 5%, more preferably less than 2%, of cannabinoids are decarboxylated during the process.

In yet another aspect, provided herein, the stability of cannabinoids in the lipid phase is significantly increased by maintaining at least 90% of cannabinoid content after two weeks at room temperature.

In yet another aspect, provided herein, is a lipid-soluble extract obtainable from the process according to the invention, wherein the extract has a terpenoid content of at least 75% of the initial plant material content in weight.

In yet another aspect, provided herein, is a lipid-soluble extract obtainable from the process according to the invention, wherein the monoterpenes content is at least 30% of the total terpenes content.

In yet another aspect, provided herein, lipids can be vegetable oils and/or glycerine and/or any other green (made from renewable sources) and/or food grade solvents.

In yet another aspect, provided herein, is a solid extract or phase of cannabis or hemp plant material obtainable from the process according to the present invention, wherein the cannabinoid content of the plant material is reduced by at least 75, 80 or preferably 90 weight percent.

In yet another aspect, provided herein, is the use of the solid extract or phase of cannabis or hemp plant material obtainable from the process according to the present invention for the formulation of food or feed materials.

In a further aspect, the aqueous phase can be used in the production of nutraceutical, antimicrobial, antibacterial products or biopesticides.

In yet another aspect, provided herein, is the use of the lipid-soluble extract for the preparation of a cream containing at least 0.5% of cannabinoids showing an increased cannabinoids stability of at least 90% of initial content after 10 weeks.

In yet another aspect, provided herein, is the use of the lipid-soluble extract for the preparation of a gummy containing at least 0.5% of cannabinoids exhibiting an increased cannabinoids stability of at least 90% of initial content after 10 weeks.

In yet another aspect, provided herein, is the use of the lipid-soluble extract for the preparation of a gel containing at least 0.5% of cannabinoids exhibiting an increased cannabinoids stability of at least 90% of initial content after 10 weeks.

In yet another aspect, provided herein, a liposome based material containing at least 0.5% of cannabinoids is described exhibiting an increased cannabinoids stability of at least 90% of initial content after 10 weeks.

DETAILED DESCRIPTION OF THE INVENTION

The present invention discloses a safe, environmental friendly and convenient method for an efficient lipid-based extraction of phyto-cannabinoids and terpenes/terpenoids.

The present invention discloses a process for producing a lipid-soluble extract from plant material containing phyto-cannabinoids, comprising the steps of:
  a. comminuting the plant material;
  b. mixing the comminuted plant material with enzymes to form a mixture to which water and lipids or solvents can be optionally added;
  c. agitating the mixture at a temperature range of 1 to 80° C.; and
  d. separating the mixture into a lipid phase, an aqueous phase, and a solid phase;
  wherein the lipid phase comprises the lipid-soluble extract.

The present invention further discloses a process for producing a lipid-soluble extract containing cannabinoids and/or terpenes/terpenoids from plant material, chosen from the group consisting of hemp, cannabis, hops, echinacea, salvia dinivorum, chrysanthemum, helichrysum and hypericum biomass, comprising the steps of:
  a. comminuting the plant material;

b. mixing the comminuted plant material with enzymes to form a mixture to which water and lipids or solvents can be optionally added;

c. agitating the mixture at a temperature range of 1 to 80° C.; and d. separating the mixture into a lipid phase, an aqueous phase, and a solid phase;

wherein the lipid phase comprises the lipid-soluble extract.

The lipid fraction generated has a phyto-cannabinoid (i.e. CBD, CBD-A, THC, THC-A) content of at least 0.1%, preferably 2%, more preferably 3%, still more preferably at least 4%. The phyto-cannabinoids containing plant material such as hemp or cannabis can be fresh or dried. Plant material is comminuted to increase the surface contact. Then water, enzymes and oil are added to the plant material to form a homogeneous mixture or slurry; temperature and pH conditions might vary according to the specific enzyme or enzymatic cocktail used to dissolve the plant material. The mixture may be agitated through stirring or other agitation methods for at least 30 min to let the enzymes degrade the plant material. Ultrasound/sonication or microwaves or steam explosion may be used before or after adding enzymes to the mixture to reduce the time necessary to achieve plant material dissolution and high cannabinoids lipid-extraction yield. Water to plant ratio is critical to achieve plant material degradation through enzymatic activity; newly harvested plant material can also be used directly, avoiding pre-drying step during which degradation and/or losses of phyto-cannabinoids and terpenes, especially monoterpenes, can occur; in such case, little to no water can be used. Lipids can be added to the mixture any time without significantly modifying enzymatic activity; a suitable lipids-to-plant material ratio to obtain high phyto-cannabinoid content and high extraction yield (at least 70%, preferably at least 80%, more preferably at least 90%) is in the range of 50 to 200%, preferably 50 to 150%. The mixture obtained is then separated via density separation (i.e. centrifugation) or pressing (French press) and/or filtration to recover a lipid fraction highly enriched with cannabinoids and waxes free. In case of lipid extract obtained from cannabis, the extract can be heated to decarboxylate acid form cannabinoids to the desired extent.

Surprisingly it has been found that the use of enzymes drastically enhances the lipid-based extraction of phyto-cannabinoids and terpenes/terpenoids, including volatile monoterpenes, allowing for a significant reduction of the lipid solvent-to-plant material ratio (i.e. 10-15 times compared to traditional Romano-Hazekamp method), while still achieving a high cannabinoids extraction yield (i.e. 90%), hence the possibility to safely and directly obtain a waxes-free lipid extract, having a phyto-cannabinoid and terpene content appropriate for and compatible with therapeutic applications dosage, where the terpene fingerprint of the plant material is faithfully reproduced. Furthermore, it has also been found that the use of enzymes dramatically increases the stability of phyto-cannabinoids and terpenes/terpenoids in the extract, allowing to achieve a shelf-life appropriate for and compatible with pharmaceutical applications with no addition of preservatives.

In addition to that, the solid fraction generated by the process shows a phyto-cannabinoids content significantly reduced. In the case of hemp seeds, the cannabinoids content was greatly reduced compared to mechanical expeller, therefore making the protein-rich solid fraction compliant with safety guidelines for feed and food product applications.

Aspects of embodiments of the present disclosure are described in greater detail below.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "cannabinoids" includes, but is not limited to, cannabinol (CBN), cannabinolic acid (CBNA), $\Delta(9)$-tetrahydrocannabinol ($\Delta(9)$-THC), $\Delta(9)$-tetrahydrocannabinolic acid ($\Delta(9)$-THCA), $\Delta(9)$-cannabidiol ($\Delta(9)$-CBD), $\Delta(9)$-tetrahydrocannabidiolic acid ($\Delta(9)$-CBDA), $\Delta(8)$-tetrahydrocannabinol ($\Delta(8)$-THC), $\Delta(8)$-tetrahydrocannabinolic acid ($\Delta(8)$-THCA), $\Delta(8)$-tetrahydrocannabidiol ($\Delta(8)$-CBD), $\Delta(8)$-tetrahydrocannabidiolic acid ($\Delta(8)$-CBDA), $\Delta(9)$-tetrahydrocannabivarin ($\Delta(9)$-THV), cannabigerol (CBG), cannabigerolic acid (CBGA), cannabichromene (CBC), cannabichromenic acid (CBCA), cannabicyclol (CBL), cannabicyclolic acid (CBLA), Cannabidivarin (CBDV) and Tetrahydrocannabivarin (THCV).

N-alkylamides includes, but is not limited to, dodeca-2E, 4E,8Z,10Z-tetraenoic acid isobutylamide and dodeca-2E, 4E-dienoic acid isobutylamide.

As used herein, the term "phyto-cannabinoids" includes, but is not limited to, cannabinoids from Cannabis and N-alkylamides from Echinacea.

As used herein, the term "terpenes" includes, but is not limited to, pinene, limonene, α-terpinene, terpinen-4-ol, carvacrol, carvone, 1,8-cineole, p-cymene, fenchone, β-myrcene, cannaflavin A, cannaflavin B, nerolidol, phytol and squalene.

As used herein, the term "terpenoids" includes, but is not limited to, cannabinoids, limonene oxide, pulegone-1,2 epoxide, salviorin A, hyperforin, and pyrethrins.

As used herein, the term "lipids" includes, but is not limited to, of olive oil, coconut oil, vegetable oil, milk, butter, liposomes, glycerine, polyethylene glycol, ethyl acetate, d-limonene, butylene glycol, propylene glycol, ethylhexyl palmitate.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

Process and Compositions:

In an aspect, provided herein, is a process for producing a lipid-soluble extract containing cannabinoids and terpenoids from cannabis or hemp plant material or from plant material containing phyto-cannabinoids and/or terpenes/terpenoids, comprising the steps of:

a. comminuting the plant material;
b. mixing the comminuted plant material with enzymes to form a mixture to which water and lipids are optionally added;
c. agitating the mixture at a temperature range of 1 to 80° C.; and
d. separating the mixture into a lipid phase, an aqueous phase, and a solid phase; wherein the lipid phase comprises the lipid-soluble extract.

In a preferred aspect, in the process according to the present invention said cannabis or hemp plant material is chosen from the group consisting of buds, flowers, leaves, stalks, stems, roots and seeds or a mixture thereof. In an embodiment, the plant material includes seeds. In another embodiment, when the plant material includes seeds, no lipid is added. In a further embodiment, when the plant material includes seeds, a lipid is added. Plant material including seeds may be rich in lipids, and thus may not need the further addition of lipids.

In an embodiment, the plant material is a mix comprising buds, flowers, leaves, stalks, stems, roots, and seeds. In another embodiment, when the plant material is a mix comprising buds, flowers, stalks, stems, leaves, roots and seeds, a lipid is added to achieve optimal lipid-to-plant material ratio for effective cannabinoids extraction. In a further embodiment, when the plant material is a mix comprising seeds, buds, flowers, stalks, stems, roots and leaves, a lipid is not added.

In an embodiment, the plant material is newly harvested and contain high level of moisture; in such case addition of extra water to the plant material is unnecessary.

In an embodiment, the plant material has a lipid content of at least 1 percent weight.

In another embodiment, the addition of lipids achieves a lipid content of at least 5 weight percent of the mixture.

In a preferred aspect, in the process according to the present invention said plant material containing phyto-cannabinoids derives from cannabis, echinacea or hemp plants which are pure, hybrids or genetically modified variants thereof.

In a still preferred aspect, in the process according to the present invention said plant material derives from the *Cannabis* genus of plants, that encompasses the species *C. sativa, C. indica* and *C. ruderalis*. Said cannabis or hemp plant material is preferably industrial hemp of the species *C. sativa*.

In a still preferred aspect, in the process according to the present invention said plant material derives from the Cannabinaceae genus of plants, that encompass the species *Cannabis* and *Humulus lupulus*.

In a still preferred aspect, in the process according to the present invention said plant material derives from the *Echinacea* genus of plants, that encompass the species *E. purpurea, E. angustifolia, E. pallida*.

In a still preferred aspect, in the process according to the present invention said plant material derives from *Chrysanthemum* genus, that encompass the species *Tanacetum cinerariifolium* and *Chrysanthemum coccineum*.

In a still preferred aspect, in the process according to the present invention said plant material derives from *Salvia divinorium*.

In a still preferred aspect, in the process according to the present invention said plant material derives from a mixture of different plant materials containing different terpenes/terpenoids.

In an embodiment, in the process according to the present invention said plant material contains at least 0.1, 1 or 2% phyto-cannabinoids in weight.

In an embodiment, in the process according to the present invention said plant material contain at least 0.5% terpenoids in weight.

In an embodiment, the plant material is hemp comprising less than 0.2%-0.6% THCtot.

In yet another embodiment, the plant material is cannabis comprising more than 0.2%-0.6% THCtot.

In a further embodiment, the plant material is a hybrid or genetically modified variant of hemp.

In yet another embodiment, the plant material is a hybrid or genetically modified variant of cannabis.

In a further aspect, in the process according to the present invention said plant material has a moisture content of at least 20%, preferably at least 30%. Furthermore, the plant material preferably has a total cannabinoid content greater than 0.2%, preferably more than 1%.

In an embodiment, the enzyme is one or more enzymes independently selected from the group consisting of cellulase, beta-glucosidase, hemicellulase, xylanase, glucanase, beta-glucanase, pectinase, amylase, alpha-amylase, phospholipase, beta-mannanase, arabinanase, phytase and protease. In an embodiment, the enzyme is cellulose. In another embodiment, the enzyme is beta-glucosidase. In another embodiment, the enzyme is hemicellulase. In another embodiment, the enzyme is xylanase. In yet another embodiment, the enzyme is glucanase. In yet another embodiment, the enzyme is pectinase. In still another embodiment, the enzyme is amylase. In yet another embodiment, the enzyme is phospholipase. In yet another embodiment, the enzyme is arabinanase. In still another embodiment, the enzyme is phytase. In a further embodiment, the enzyme is protease.

In a preferred embodiment, the enzyme is a mix or a cocktail of cellulase, beta-glucanase, pectinase, beta-mannanase, alpha-amylase and protease; wherein the amount of enzyme is 3% of the weight of plant material; and the pH of the mixture is adjusted to pH 5.6 with monohydrate citric acid.

In an embodiment, the amount of enzyme is in the range of from 0.2%, 0.5% to 10% of the weight of plant material. In another embodiment, the pH of the mixture is 3-10. In a particular embodiment, the enzyme concentration and pH level of the mixture produce optimal enzymatic activity.

In an embodiment, the lipid is one or more lipids independently selected from the group consisting of olive oil, coconut oil, sesame oil, vegetable oil, milk, butter, liposomes and hemp seed oil and/or other green and/or food grade solvents such as glycerine, polyethylene glycol, ethyl acetate, d-limonene, butylene glycol, propylene glycol, ethylhexyl palmitate and/or with the addition of lecithin. In an embodiment, the lipid is olive oil. In another embodiment, the lipid is coconut oil. In another embodiment, the lipid is sesame oil. In another embodiment, the lipid is vegetable oil. In yet another embodiment, the lipid is milk. In a further embodiment, the lipid is butter.

In an embodiment, the weight ratio of lipid to plant material is in the range of 0.01:1 to 4:1 and the weight ratio of water to plant material is in the range of 0.01:1 to 10:1. In another embodiment, the weight ratio of lipid to plant material is in the range of 0.1:1 to 2:1 and the weight ratio of water to plant material is in the range of 1:1 to 5:1. In a particular embodiment, the weight ratio of lipid to plant material is in the range of 0.5:1 to 1.5:1 and the weight ratio of water to plant material is in the range of 2:1 to 3:1. The weight ratio of lipid to plant material is preferably in the range of 2:3 and the weight ration of water to plant material in dry matter is in the range of 0.01:1 to 10:1, preferably in the range of 2:1.

In an embodiment, the mixture is treated with ultrasound prior to the addition of the enzymes. In an embodiment, the mixture is treated with microwaves prior to the addition of the enzymes.

In an embodiment, the mixture is treated with ultrasound after to the addition of the enzymes. In an embodiment, the mixture is treated with microwaves after to the addition of the enzymes.

In an embodiment, the lipids, water and enzymes are added in any different combinations of order.

In a particular embodiment, the commuting the plant matter, adding the lipids, adding the water and adding the enzymes is done in any different combination of order.

In an embodiment, the mixture is agitated for at least 10 minutes, preferably 30 or 60 minutes.

In an embodiment, the mixture is agitated at a temperature range of 40 to 70° C.

In an embodiment, the mixture is separated by density. In a further embodiment, the mixture is separated by pressing and/or filtering.

In a further embodiment, the mixture is separated into a lipid phase and a wet solid phase.

In an embodiment, the lipid-soluble extract is recirculated any number of times to achieve higher cannabinoid or terpene content.

In an embodiment, the lipid-soluble extract is recirculated any number of times to achieve higher cannabinoid or terpene stability.

In a further embodiment, at least 50%, preferably 70% of the terpenoids, at least 70% of the diterpenoids and at least 50%, preferably 70% of monoterpenes contained in the plant material are extracted into the lipid-soluble extract.

In a still further embodiment at least 70% of the sesquiterpenes and at least 50% of the monoterpenes contained in the plant material are extracted into the lipid-soluble extract.

In an embodiment, the lipid-soluble extract has a total cannabinoid content of at least 2 weight percent. In a further embodiment, the lipid-based extract has a total cannabinoid content of at least 3 weight percent. In yet another embodiment, the lipid-based extract has a total cannabinoid content of at least 5 weight percent.

In an embodiment, the two main cannabinoids in the lipid-soluble extract are preferably THC and CBD, or any other cannabinoids.

In a further embodiment, the invention provides a lipid-soluble extract obtainable from the process for producing a lipid-soluble extract containing cannabinoids and terpenoids from plant material, chosen from the group consisting of hemp, cannabis, hops, echinacea, salvia dinivorum, chrysanthemum, helichrysum and hypericum biomass and *Tanacetum cinerariifolium* plant material, comprising the steps of:

a. comminuting the plant material;
b. mixing the comminuted plant material with enzymes to form a mixture to which water and lipids are optionally added;
c. agitating the mixture at a temperature range of 1 to 80° C.; and
d. separating the mixture into a lipid phase, an aqueous phase, and a solid phase;
wherein the lipid phase comprises the lipid-soluble extract.

The extract is surprisingly stable 60 days after extraction.

Preferably in the lipid-soluble extract the degradation of cannabinoids after four weeks in darkness at 25° C. is less than 5% and has a total cannabinoid content of at least 90%, preferably at least 95%, the ratio between the two main cannabinoids in the lipid-soluble extract differs for less than 10%, preferably less than 5%, the ratio between the two main cannabinoids in the plant material, and less than 10%, preferably less than 5%, more preferably less than 2%, of cannabinoids are decarboxylated during the process, and the ratio monoterpenes/diterpenes after four weeks in darkness at 25° C. is less than 5%, and the monoterpenes content is at 80% of the initial content.

In yet another aspect, provided herein, is a lipid-soluble extract obtainable from the process according to the invention, wherein the fingerprint of plant material is reproduced in the extract, meaning that the variation of the ratio of the two main cannabinoids compared to the ratio of the starting plant material is below 10%.

In a further embodiment, the ratio THCtot:CBDtot in the lipid-soluble extract differs for less than 5% the THCtot:CBDtot in the plant material.

In yet another aspect, provided herein, is a lipid-soluble extract obtainable from the process according to the invention, wherein decarboxylated forms of cannabinoids represent less than 10% of the total cannabinoids content.

In yet another aspect, provided herein, the stability of cannabinoids in the lipid phase is significantly increased by maintaining at least 90% of cannabinoids content after two weeks at room temperature and in dark.

In yet another aspect, provided herein, is a lipid-soluble extract obtainable from the process according to the invention, wherein the extract has a terpenes/terpenoid content of at least 75% of the initial plant material content in weight.

In yet another aspect, provided herein, is a lipid-soluble extract obtainable from the process according to the invention, wherein the monoterpenes content is at least 30% of the total terpenes content.

The lipid-soluble extract according to the invention surprisingly has a cannabinoid content of
DELTA-9-TETRAHYDROCANNABINOL (THC-ACID): in a range of from 1,000 to 6,000 mg/kg
DELTA-9-TETRAHYDROCANNABINOL (THC-NEUTRAL): in a range of from 100 to 500 mg/kg
DELTA-9-TETRAHYDROCANNABINOL (THC-TOTAL EXPRESSED AS THC NEUTRAL): in a range of from 1,000 to 7,000 mg/kg
CANNABIDIOL (CBD): in a range of from 1,000 to 5,000 mg/kg
CANNABIDIOL ACID (CBD-A): in a range of from 20,000 to 80,000 mg/kg.

In an embodiment, the plant material is heated before forming the mixture for cannabinoids decarboxylation. In an embodiment, the mixture is heated for cannabinoids decarboxylation. In an embodiment, the lipid extract is heated for cannabinoids decarboxylation.

In an embodiment, the cannabinoid content of the solid phase is reduced by at least 75 weight percent. In another embodiment, the cannabinoid content of the solid phase is reduced by at least 80 weight percent. In a further embodiment, the cannabinoids content of the solid phase is reduced by at least 90 weight percent.

In an embodiment, the solid phase and the lipid-soluble extract are used for the formulation of food and feed products.

In another embodiment, the aqueous phase and the lipid-soluble extract are used in the production of pharmaceutical, nutraceutical products, cosmetics, food or feed products, antimicrobial, antibacterial, insecticidal, or biocidal products.

In another aspect, provided herein, is a lipid-soluble extract, wherein the extract has a total phyto-cannabinoid content of at least 5 weight percent.

In an embodiment, the plant material includes seeds. In another embodiment, when the plant material includes seeds, no lipid is added. In a further embodiment, when the plant material includes seeds, a lipid is added.

In an embodiment, the plant material is a mix comprising buds, flowers, stalks, stems, leaves, roots, and seeds. In another embodiment, when the plant material is a mix comprising buds, flowers, stalks, stems, leaves, roots and seeds, a lipid is added to achieve optimal lipid-to-plant material ratio for effective cannabinoids extraction. In a further embodiment, when the plant material is a mix comprising buds/flowers and seeds, a lipid is not added.

In an embodiment, the plant material is newly harvested and contains high level of moisture; in such case addition of extra water to the plant material is unnecessary.

In an embodiment, the plant material has a lipid content of at least 1 weight percent.

In another embodiment, the addition of lipids achieves a lipid content of 5 weight percent of the mixture.

In an embodiment, the mixture is agitated for at least 10 mintues.

In an embodiment, the mixture is separated by density. In a further embodiment, the mixture is separated by pressing and filtering.

In an embodiment, the mixture is agitated at a temperature rang of 40 to 70° C.

In an embodiment, the plant material is hemp comprising less than 0.6% THCtot. In yet another embodiment, the plant material is cannabis comprising more than 0.6% THCtot. In a further embodiment, the plant material is a hybrid or genetically modified variant of hemp. In yet another embodiment, the plant material is a hybrid or genetically modified variant of cannabis.

In an embodiment, the enzyme is one or more enzymes independently selected from the group consisting of cellulase, beta-glucosidase, hemicellulase, xylanase, glucanase, pectinase, amylase, phospholipase, beta-mannanase, arabinanase, phytase and protease. In an embodiment, the enzyme is cellulase. In another embodiment, the enzyme is beta-glucosidase. In another embodiment, the enzyme is hemicellulase. In another embodiment, the enzyme is xylanase. In yet another embodiment, the enzyme is glucanase. In yet another embodiment, the enzyme is pectinase. In still another embodiment, the enzyme is amylase. In yet another embodiment, the enzyme is phospholipase. In yet another embodiment, the enzyme is beta-mannanase. In yet another embodiment, the enzyme is arabinanase. In still another embodiment, the enzyme is phytase. In a further embodiment, the enzyme is protease.

In an embodiment, the amount of enzyme is 0.5% to 10%, preferably 3%, of the weight of plant material. In another embodiment, the pH of the mixture is 3-10, preferably pH 5.6. In a particular embodiment, the enzyme concentration and pH level of the mixture produce optimal enzymatic activity.

In an embodiment, the lipid is one or more lipids independently selected from the group consisting of olive oil, coconut oil, sesame oil, vegetable oil, milk, butter, liposomes, hemp seed oil and/or other green and/or food grade solvents such as glycerine, polyethylene glycol, ethyl acetate. In an embodiment, the lipid is olive oil. In another embodiment, the lipid is coconut oil. In another embodiment, the lipid is vegetable oil. In yet another embodiment, the lipid is milk. In a further embodiment, the lipid is butter.

In an embodiment, the weight ratio of lipid to plant material is in the range of 0.01:1 to 4:1 and the weight ratio of water to plant material is in the range of 0.01:1 to 10:1. In another embodiment, the weight ratio of lipid to plant material is in the range of 0.1:1 to 2:1 and the weight ratio of water to plant material is in the range of 1:1 to 5:1. In a particular embodiment, the weight ratio of lipid to plant material is in the range of 0.5:1 to 1:1.5 and the weight ratio of water to plant material is in the range of 2:1 to 3:1.

In an embodiment, the mixture is treated with ultrasound prior to the addition of the enzymes. In an embodiment, the mixture is treated with microwaves prior to the addition of the enzymes.

In an embodiment, the mixture is treated with ultrasound after to the addition of the enzymes. In an embodiment, the mixture is treated with microwaves after to the addition of the enzymes.

In an embodiment, the lipids, water and enzymes are added in any different combinations of order.

In a particular embodiment, the commuting the plant matter, adding the lipids, adding the water and adding the enzymes is done in any different combination of order.

In an embodiment, the lipid-soluble extract is recirculated any number of times to achieve higher phyto-cannabinoid content.

In an embodiment, the lipid-soluble extract is recirculated any number of times to achieve higher phyto-cannabinoid stability.

In an embodiment, the lipid-soluble extract has a total phyto-cannabinoid content of at least 2 weight percent. In a further embodiment, the lipid-based extract has a total cannabinoid content of at least 3 weight percent. In yet another embodiment, the lipid-based extract has a total cannabinoid content of at least 5 weight percent.

In an embodiment, the plant material is heated before forming the mixture for cannabinoids decarboxylation. In an embodiment, the mixture is heated for cannabinoids decarboxylation. In an embodiment, the lipid-soluble extract is heated for cannabinoids decarboxylation.

In an embodiment, the phyto-cannabinoid content of the solid phase is reduced by at least 75 weight percent. In another embodiment, the phyto-cannabinoid content of the solid phase is reduced by at least 80 weight percent. In a further embodiment, the phyto-cannabinoid content of the solid phase is reduced by at least 90 weight percent.

In an embodiment, the solid phase is used for the formulation of food and feed products.

In another embodiment, the aqueous phase can be used in the production of nutraceutical products, antimicrobial, antibacterial or biopesticides.

In yet another aspect, provided herein, is a solid extract of cannabis or hemp plant material, wherein the cannabinoid content of the plant material is reduced by at least 90 weight percent.

In an embodiment, the wherein the solid phase or extract are made by a process for producing a lipid-soluble extract containing cannabinoids and terpenes from plant material, chosen from the group consisting of hemp, cannabis, hops, echinacea, salvia dinivorum, chrysanthemum, helichrysum and hypericum biomass, comprising the steps of:

a. comminuting the plant material;

b. mixing the comminuted plant material with water, enzymes and lipids to form a mixture;

c. agitating the mixture at a temperature range of 1 to 80° C.; and d. separating the mixture into a lipid phase, an aqueous phase, and a solid phase;

wherein the lipid phase comprises the lipid-soluble extract.

In an embodiment, the plant material includes seeds. In another embodiment, when the plant material includes seeds, no lipid is added. In a further embodiment, when the plant material includes seeds, a lipid is added.

In an embodiment, the plant material is a mix comprising buds, flowers, stalks, stems, leaves, roots and seeds. In another embodiment, when the plant material is a mix comprising buds, flowers, stalks, stems, leaves, roots and seeds, a lipid is added to achieve optimal lipid-to-plant material ratio for effective cannabinoids extraction. In a further embodiment, when the plant material is a mix comprising seeds and buds, flowers, stalks, stems, leaves, roots and seeds, a lipid is not added.

In an embodiment, the plant material has a seed content of less than 98% of the plant material weight and the plant material other than (different from) seeds is greater than 2% of the plant material weight.

In an embodiment, the plant material has a lipid content of at least 1 weight percent of the plant material.

In another embodiment, the addition of lipids achieves a lipid content of 5 weight percent of the mixture.

In an embodiment, the mixture is agitated for at least 10, preferably 30 minutes.

In an embodiment, the mixture is separated by density. In a further embodiment, the mixture is separated by pressing and filtering.

In an embodiment, the mixture is agitated at a temperature rang of 40 to 75° C., preferably 55° C.

In an embodiment, the plant material is hemp comprising less than 0.6% THC. In yet another embodiment, the plant material is cannabis comprising more than 0.6% THC. In a further embodiment, the plant material is a hybrid or genetically modified variant of hemp. In yet another embodiment, the plant material is a hybrid or genetically modified variant of cannabis.

In an embodiment, the enzyme is one or more enzymes independently selected from the group consisting of cellulase, beta-glucosidase, hemicellulase, xylanase, glucanase, pectinase, amylase, phospholipase, beta-mannanase, arabinanase, phytase and protease. In an embodiment, the enzyme is cellulose. In yet another embodiment, the enzyme is beta-glucosidase. In another embodiment, the enzyme is hemicellulase. In another embodiment, the enzyme is xylanase. In yet another embodiment, the enzyme is glucanase. In yet another embodiment, the enzyme is pectinase. In still another embodiment, the enzyme is amylase. In yet another embodiment, the enzyme is phospholipase. In yet another embodiment, the enzyme is beta-mannanase. In yet another embodiment, the enzyme is arabinanase. In still another embodiment, the enzyme is phytase. In a further embodiment, the enzyme is protease.

In an embodiment, the amount of enzyme is 0.5% to 10% of the weight of plant material. In another embodiment, the pH of the mixture is 3-10. In a particular embodiment, the enzyme concentration and pH level of the mixture produce optimal enzymatic activity.

In an embodiment, the lipid is one or more lipids independently selected from the group consisting of olive oil, coconut oil, vegetable oil, milk, hemp seed oil and butter. In an embodiment, the lipid is olive oil. In another embodiment, the lipid is coconut oil. In another embodiment, the lipid is vegetable oil. In yet another embodiment, the lipid is milk. In still another embodiment, the lipid is glycerine. In a further embodiment, the lipid is butter.

In an embodiment, the weight ratio of lipid to plant material is in the range of 0.01:1 to 4:1 and the weight ratio of water to plant material is in the range of 0.01:1 to 10:1. In another embodiment, the weight ratio of lipid to plant material is in the range of 0.1:1 to 2:1 and the weight ratio of water to plant material is in the range of 1:1 to 5:1. In a particular embodiment, the weight ratio of lipid to plant material is in the range of 0.5:1 to 1:1.5 and the weight ratio of water to plant material is in the range of 2:1 to 3:1.

In an embodiment, the mixture is treated with ultrasound prior to the addition of the enzymes. In an embodiment, the mixture is treated with microwaves prior to the addition of the enzymes.

In an embodiment, the mixture is treated with ultrasound after to the addition of the enzymes. In an embodiment, the mixture is treated with microwaves after to the addition of the enzymes.

In an embodiment, the lipids, water and enzymes are added in any different combinations of order.

In a particular embodiment, the commuting the plant matter, adding the lipids, adding the water and adding the enzymes is done in any different combination of order.

In an embodiment, the lipid-soluble extract is recirculated any number of times to achieve higher cannabinoid content.

In an embodiment, the lipid-soluble extract has a total cannabinoid content of at least least 2 weight percent. In a further embodiment, the lipid-based extract has a total cannabinoid content of at least 3 weight percent. In yet another embodiment, the lipid-based extract has a total cannabinoid content of at least 5 weight percent.

In an embodiment, the plant material is heated before forming the mixture for cannabinoids decarboxylation. In an embodiment, the mixture is heated for cannabinoids decarboxylation. In an embodiment, the lipid-soluble is heated for cannabinoids decarboxylation.

In an embodiment, the cannabinoid content of the solid phase obtainable from the process according to the present invention is reduced by at least 75 weight percent. In another embodiment, the cannabinoid content of the solid phase is reduced by at least 80 weight percent.

In a further embodiment, the cannabinoid content of the solid phase is reduced by at least 90 weight percent.

In an embodiment, the solid phase is used for the formulation of food and feed products.

In another embodiment, the aqueous phase can be used in the production of nutraceutical products, antimicrobial, antibacterial or biopesticides.

In yet another aspect, provided herein, is the use of the solid extract or phase of cannabis or hemp plant material obtainable from the process according to the present invention for the formulation of food or feed materials.

In a further aspect, the aqueous phase can be used in the production of nutraceutical, antimicrobial, antibacterial products or biopesticides.

In yet another aspect, provided herein, is the use of the lipid-soluble extract for the preparation of a cream or gel containing at least 0.5% of cannabinoids showing an increased cannabinoids stability of at least 90% of initial content after 10 weeks.

In yet another aspect, provided herein, is the use of the lipid-soluble extract for the preparation of a gummy or candy containing at least 0.5% of cannabinoids exhibiting an increased cannabinoids stability of at least 90% of initial content after 10 weeks.

In yet another aspect, provided herein, is the use of the lipid-soluble extract for the preparation of a gel containing at least 0.5% of cannabinoids exhibiting an increased cannabinoids stability of at least 90% of initial content after 10 weeks.

In a still further aspect, the use of the aqueous phase obtainable from the process according to the invention, for the preparation of pharmaceutical or nutraceutical products, cosmetics, food or feed products, antimicrobial, antibacterial, insecticidal or biopesticides.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1

150 g of dried industrial hemp buds, comprising a small quantity of seeds, variety Futura 75 were mixed in a kitchen aid stirrer Mulinex Companion with 340 g of water, 100 g of extra-virgin olive oil offered by Azienda Agricola Montesoli, Siena. The temperature of the mixture was brought and kept to 55° C. with constant stirring at 100 rpm for 3.5 h. The mixture was then centrifuged at 11.000 rpm for 10 min. No lipid extract could be obtained as the lipids remained adsorbed in the vegetable matrix. The process was then repeated with the only difference of adding to the mixture a cocktail of commercial food-grade enzymes and adjusting the pH to pH 5.6 with 6 g of monohydrate citric acid. The enzymatic cocktail comprised Celluclast 1.5 L (cellulase), Ultraflow Max (betaglucanase), Peclyve (pectinase, beta-glucanases, cellulases, and beta-mannanases) and Ceremix 2XL (Alpha-amylase, Beta-glucanase, Protease). Total enzymes concentration was 3% of the hemp plant material weight. After 3.5 h the mixture becomes homogeneous. After mixture centrifugation (11.000 rpm for 5 min), 91 g of lipid-soluble extract, 80 g of an intermediate aqueous phase and 410 g of a wet solid fraction were recovered. The solid fraction was dried in oven at 50° C. for 6 h. Futura 75 hemp buds and lipid extract were sent out for cannabinoids and terpenes analysis to an accredited lab. The solid fraction was analysed for cannabinoid content only.

The methodology used for cannabinoids analysis is UPLC-MS/MS, with detection limit for di THC and THC acid not less than 1.0 mg/Kg in oil and 0.10 mg/Kg in hemp flour and seeds. Δ-9-tetrahydrocannabinol and its derived acid were extracted with a mixture of methanol and dichloromethane for the solid material or another methanol based mixture for the oil. Chromatographic conditions: phase A: water+formic acid 0.1% (v/v), phase B: acetonitrile+formic acid 0.1% (v/v). Flux: 0.5 mL/min, Column: Waters® Acquity UPLC BEH C18 2.1×100 mm, 1.7 µm or equivalent. Temperature of column: 35° C. Temperature autosampling: 8° C. Spectrometer mass conditions: Temperature source: 130° C. Temperature desolventizing: 400° C. Capillar: 1 KV. Flux: 1000 L/h. Cone Flux: 50 L/h. THC total is calculated according to the following formula:

$$Ctot = Ca \times PMn/PMa = Cn$$

C tot=analyte content (THC total) in the sample analyzed, in mg/Kg
Cn=concentration of THC neutral calculated, in mg/Kg
Ca=concentration of THC acid calculated, in mg/Kg
PMa=molecular weight THC acid
PMn=molecular weight THC neutral The following cannabinoid concentrations (mg/Kg) in the buds were found:
DELTA-9-TETRAHYDROCANNABINOL (THC-ACID): 1,229
DELTA-9-TETRAHYDROCANNABINOL (THC-NEUTRAL): 142.8
CANNABIDIOL (CBD): 2,328
CANNABIDIOL ACID (CBD-A): 21,230
CANNABINOL (CBN): 10

Cannabinoid content in the lipid fraction were as follow (mg/Kg):
DELTA-9-TETRAHYDROCANNABINOL (THC-ACID): 1,983
DELTA-9-TETRAHYDROCANNABINOL (THC-NEUTRAL): 146.8
CANNABIDIOL (CBD): 3,750
CANNABIDIOL ACID (CBD-A): 23,246
CANNABINOL (CBN): 12

Considering the ratio oil-to-plant material (2 to 3), an efficiency for THC (TOTAL) of 2,130*(2/3)*0,91/1,372=94.2% was achieved. As it can be seen, a CBD content of 2.3%, even superior to the initial plant materials has been reached. Considering the test mass balance, a 93.8% cannabinoids extraction yield has been achieved, using 15 times less solvent than alternative lipid-based extraction scientific methodologies (Romano and Hazekamp, 2013; Cannazza, 2016). Furthermore, the process was able to reproduce in the extract the fingerprint of the plant material, maintaining the variation of the ratio between the two main cannabinoids CBD and THC below 5%. The ratio THCtot:CBDtot in the plant material and in the extract were 0,058 and 0,079 respectively. The variation of the ratio was therefore limited to 0.02 or 2%. Moreover, the process did not decarboxylated nor degraded cannabinoids as the unchanged ratio CBDA:CBD and THCA:THC in the plant material and in the lipid extract as well as well as the low CBN content demonstrate.

The solid fraction presented a cannabinoids content as follow (mg/Kg):
DELTA-9-TETRAHYDROCANNABINOL (THC-ACID): 21
DELTA-9-TETRAHYDROCANNABINOL (THC-NEUTRAL): 9
CANNABIDIOL (CBD): 390
CANNABIDIOL ACID (CBD-A): 5,986

As it can be noticed, a significant reduction of THC in the plant material has been achieved. The lipid extract was also analysed for terpene fingerprint. GC-MS analyses were performed in an Agilent 5973N mass selective detector coupled to an Agilent 6890 gas chromatograph (Palo Alto, Calif.), equipped with a HP5-MS capillary column (30 m×0.25 mm×0.25 µm), operating in electronic ionization mode at 70 eV, with transfer line maintained at 260° C., while quadrupole and ion source temperature were held at 150° C. and 230° C., respectively. Helium (1.0 mL min-1) was used as carrier gas. The injector temperature was kept at 250° C. and the oven temperature program was from 60° to 240° C. at a rate of 3° C. min-1. Detector (FID) was operated at 280° C. The lipid extract (0.03 µL) was injected in split mode (100:1). A standard solution of n-alkanes (C7-C26) was used to obtain the retention indices. Individual volatile components were identified by comparison of their mass spectra (MS) and retention indices (RI) with those reported in literature.

Main terpenes contained in the lipid extract were as follow:

| Compound | % |
|---|---|
| Alfa-Pinene | 14.4 |
| Beta-Pinene | 5.3 |
| Beta-Myrcene | 21.4 |
| Limonene | 5.2 |
| Terpinolene | 10.5 |
| Beta-Caryophyllene | 17.1 |
| Alfa-Humulene | 6.1 |

Terpene fingerprint of the obtained extract is well comparable with that reported by Nissen et al (2010). Taking in consideration that in our case initial plant material was dried and not newly harvested, it can be noticed that no significant variation of original fingerprint nor degradation of cannabinoids and terpenes occurred during the process.

Example 2

5 Kg of hemp seeds (oil content 34%) were processed with a mechanical screw-type expeller Bracco Srl, Italy, 7.5 kW, 50 Kg/h. Extracted oil and seedcake were analyzed for CBD-A content. Oil extracted with mechanical expeller presented a CBD-A content of 16.3 mg/Kg, while seedcake presented a CBD-A content of 17.8 mg/Kg.

200 gr of the seeds were processed using the enzyme-assisted extraction protocol of Example 1 with the only difference that no external source of oil was added as the oil was already included in the seeds. The oil extract and the solid fraction were collected. The solid fraction was dried in an oven at 50 degrees Celsius. The oil and the solid fraction were sent out for CBD-A analysis. The oil extracted with our enzyme-assisted protocol presented a CBD-A content of 21.1 mg/Kg. The dried solid fraction presented a CBD-A content of 4.3 mg/Kg.

As it can be seen, the proposed method increased the cannabinoids content in the lipid fraction, while it significantly reduced the cannabinoids content in the residual protein-rich solid fraction.

Example 3

100 g of hemp based lipid extract prepared with the process described in the previous Example, having CBD-A content of 21.3, was added to Futura 75 hemp buds in substitution to olive oil using the same protocol of Example 1. Without enzymes, no lipid extract was recovered. With enzymes, 92 grams of lipid extract were recovered. Cannabinoids content of recovered lipid extract was (mg/Kg):
DELTA-9-TETRAHYDROCANNABINOL (THC-ACID): 1,440
DELTA-9-TETRAHYDROCANNABINOL (THC-NEUTRAL): 133.2
CANNABIDIOL (CBD): 3,819
CANNABIDIOL ACID (CBD-A): 25,388

As it can be seen, using an enzymatic approach to produce an oil from hemp seeds and then use the same oil to extract hemp buds, CBD and CBD-A content achievable in the extract is even higher than the initial hemp buds content.

Example 4

Example 1 was repeated with a sonication treatment of the mixture before adding enzymes. Conditions for the treatment: 250 W of ultrasonic power, 30 min of ultrasonic time, and 50° C. of ultrasonic temperature. It was found that the ultrasonic treatment allowed for a reduction of timing from 3,5 hours to 2.5 to reach the comparable cannabinoids extraction yield described in Example 1.

Example 5

Analysis for cannabinoids content in the lipid fraction of example 1 was repeated after 21 days and after 60 days.
After 21 days, cannabinoids content was:
DELTA-9-TETRAHYDROCANNABINOL (THC-ACID): 1,935
DELTA-9-TETRAHYDROCANNABINOL (THC-NEUTRAL): 148.9
CANNABIDIOL (CBD): 3,754
CANNABIDIOL ACID (CBD-A): 23,238
After 60 days, cannabinoids content was:
DELTA-9-TETRAHYDROCANNABINOL (THC-ACID): 1,937
DELTA-9-TETRAHYDROCANNABINOL (THC-NEUTRAL): 149.8
CANNABIDIOL (CBD): 3,757
CANNABIDIOL ACID (CBD-A): 23,216
In both cases, no significant reduction in cannabinoid contents have been found.

Example 6

375 g of newly harvested fresh buds of Futura 75, having a moisture content of 60%, were treated as in example 1 with the only difference that no water was added to the mixture as initial moisture was sufficient for enzymatic activity. The same quantity of lipid extract was obtained (91 g). The lipid extract was sent out for cannabinoids and terpenes analysis. Cannabinoids content (mg/Kg):
DELTA-9-TETRAHYDROCANNABINOL (THC-ACID): 2,130
DELTA-9-TETRAHYDROCANNABINOL (THC-NEUTRAL): 126.2
CANNABIDIOL (CBD): 1,950
CANNABIDIOL ACID (CBD-A): 25,347
Terpene fingerprint was as follow:

| Compound | % |
|---|---|
| Alfa-Pinene | 16.4 |
| Beta-Pinene | 6.3 |
| Beta-Myrcene | 20.4 |
| Limonene | 5.3 |
| Terpinolene | 10.4 |
| Beta-Caryophyllene | 16.1 |
| Alfa-Humulene | 5.9 |

In such a way it has been possible to obtain not only an elevated cannabinoids extraction yield but also the extraction of the whole terpene fingerprint, including volatile monoterpenes.

Example 7

150 g of *Echinacea purpurea* (purple coneflower) dried roots were mixed in a kitchen aid stirrer Mulinex Companion with 340 g of water, 100 g of extra-virgin olive oil offered by Azienda Agricola Montesoli, Siena and a cocktail of commercial food-grade enzymes comprising Celluclast 1.5 L (cellulase), Ultraflow Max (betaglucanase), Peclyve (pectinase, beta-glucanases, cellulases, and beta-mannanases) and Ceremix 2XL (Alpha-amylase, Beta-glucanase, Protease). Total enzymes concentration was 3% of the Echinacea plant material weight. The pH of the mixture was adjusted to pH 5.6 with 6 g of monohydrate citric acid, while the temperature of the mixture was brought and kept to 55° C. with constant stirring at 100 rpm. After 3.5 h the mixture becomes homogeneous. After mixture centrifugation (11.000 rpm for 5 min), 92 g of lipid-soluble extract, 80 g of an intermediate aqueous phase and 409 g of a wet solid fraction were recovered. The lipid fraction was sent out for analysis of total N-alkylamides (N-alkamides) content by HPLC which consisted of a Beckman System Gold 126 solvent module, a Beckman model 508 autosampler, a Beckman model 168 detector (Beckman Coulter, Inc., Fullerton, Calif.), and a 250×10 mm i.d., 5 μm ODC-AM-303 RP-$C_{18}$column (YMC, Inc., Wilmington, N.C.). The HPLC method for alkamide analysis was the same as that reported by Senchina et al.

The mobile phases for the alkamide gradient were as follows: (A) degassed Milli-Q water and (B) acetonitrile. A linear gradient of increasing 40% B to 80% B was developed within 45 min at a flow rate of 1.0 mL/min with UV detection from 200 to 600 nm. The injection volume was 15 μL. All Echinacea extracts were filtered through 0.45 μm polytetrafluoroethylene filters (Alltech Associates Inc., Deerfield, Ill.) before injecting into the HPLC. Total N-alkylamides contents in the roots and lipid fractions were as follow (mg/Kg):

Roots: 3,016 mg/Kg
Lipid extract: 3,257 mg/Kg

After 4 weeks at room temperature the analysis for N-alkylamides was repeated for the lipid-soluble extract with the following result:

3,197 mg/Kg

As it can be noticed, variation of N-alkylamides content in the lipid based extract was very limited.

Example 8

150 g of *Chrysanthemum cinerariaefolium* dried flowers (content 1,2%) pyrethrin I and pyrethrin II were bought from local farms in Kenya and mixed in a kitchen aid stirrer Mulinex Companion with 340 g of water, 100 g of extra-virgin olive oil and a cocktail of commercial food-grade enzymes comprising Celluclast 1.5 L (cellulase), Ultraflow Max (betaglucanase), Peclyve (pectinase, beta-glucanases, cellulases, and beta-mannanases) and Ceremix 2XL (Alpha-amylase, Beta-glucanase, Protease). Total enzymes concentration was 3% of the Chrysanthemum plant material weight. The pH of the mixture was adjusted to pH 5.6 with 6 g of monohydrate citric acid, while the temperature of the mixture was brought and kept to 55° C. with constant stirring at 100 rpm. After 3 h the mixture becomes homogeneous. After mixture centrifugation (11.000 rpm for 5 min), 94 g of lipid-soluble extract, 81 g of an intermediate aqueous phase and 405 g of a wet solid fraction were recovered. The initial plant material and the lipid extract were sent out for analysis of Pyrethryns content by HPLC using a Beckman System Gold 126 solvent module, a Beckman model 508 autosampler, a Beckman model 168 detector (Beckman Coulter, Inc., Fullerton, Calif.), and a 250×10 mm i.d., 5 μm ODC-AM-303 RP-C18column (YMC, Inc., Wilmington, N.C.). The HPLC method for pyrethryns analysis was the same as proposed by Marr. Elution was conducted with a mixture of acetyl acetate and hexane in a ratio of 1:10 at a constant flow rate of 1.5 ml per minute, leading to a 15-min analysis. The UVdetector was set at 242 nm wavelength. A refined pyrethrin sample was bought from RdH laborchemikalien & Co. KG (Germany) for standardization of the analytic method.

Its pyrethrin content was claimed to be 21.1%.
Total pyrethrin content (Pyrethryin I and II) was 1,4%. Ratio Pyrethryn I to Pyrethryn II was 1,65.

After 4 weeks in darkness at room temperature the analysis for pyrethryns was repeated for the lipid-soluble extract. Pyrethryns content was 1,37% mg/Kg while the ratio Pyrethryin I to Pyrethryn II was 1,68.

As it can be noticed, not only extraction was very efficient but also stability of pyrethryns in the lipid extract was significant.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A process for producing a lipid-soluble extract from plant material containing phyto-cannabinoids and/or terpenoids and/or terpenes, comprising the steps of:
   a. comminuting the plant material;
   b. mixing the comminuted plant material with enzymes to form a mixture to which water and lipids are added;
   c. agitating the mixture at a temperature range of 1 to 80° C.; and
   d. separating the mixture into alipid phase, an aqueous phase, and a solid phase; wherein the lipid phase comprises the lipid-soluble extract.

2. The process according to claim 1, wherein lipids are added to said mixing step b.

3. The process of claim 1, wherein water is added to said mixing step b.

4. The process according to claim 1, wherein said plant material is chosen from the group consisting of buds, flowers, leaves, stalks, stems, roots and seeds or a mixture thereof.

5. The process according to claim 1, wherein said plant material containing phyto-cannabinoids or terpenoids is chosen from the group consisting of hemp, cannabis, hops, echinacea, *Salvia divinorum*, chrysanthemum, *Helichrysum* spp., and *Hypericum* spp., biomass and wherein said plants are naturally occurring, or hybrids or genetically modified variants thereof.

6. The process according to claim 1, wherein said plant material derives from the *Cannabis* genus of plants, that encompasses the species *C. sativa, C. indica* and *C. ruderalis*.

7. The process according to claim 1, wherein said enzymes of step b. are one or more enzymes independently selected from the group consisting of cellulase, hemicellulase, xylanase, glucanase, beta-glucanase, pectinase, amylase, alpha-amylase, beta-amylase, phospholipase, arabanase, galacto-, beta-mannanase, protease and phytase.

8. The process according to claim 1, wherein the mixture is agitated at a temperature range of 40 to 75° C.

9. The process according to claim 1, wherein the enzyme is one or more enzymes independently selected from the group consisting of cellulase, hemicellulase, xylanase, glucanase, beta-glucanase, pectinase, amylase, alpha-amylase, phospholipase, arabanase, galacto-, beta-mannanase, protease and phytase; wherein the amount of enzyme is 0.5% to 10% of the weight of plant material; and the pH of the mixture is 3-10.

10. The process according to claim 1, wherein the lipid is one or more green and/or food grade solvents independently selected from the group consisting of olive oil, coconut oil, sesame oil, vegetable oil, milk, butter, liposomes, ethyl acetate, glycerine, d-limonene, butylene glycol, propylene glycol, polyethylene glycol, lecithin, ethylhexyl palmitate and hemp seed oil or a mixture thereof.

11. The process according to claim 1, wherein the weight ratio of lipid to plant material in dry matter is in the range of 0.01:1 to 4:1, and the weight ratio of water to plant material in dry matter is in the range of 0.01:1 to 10:1.

12. The process according to claim 1, wherein the mixture is treated with ultrasound or microwaves prior to the addition of the enzymes.

13. The process according to claim 1, wherein step b, is performed before step a.

\* \* \* \* \*